United States Patent
Li et al.

(10) Patent No.: US 6,891,155 B2
(45) Date of Patent: May 10, 2005

(54) DIELECTRIC FILM (75) Inventors: Jie Li, Ithaca, NY (US); Thomas N. Corso, Lansing, NY (US); Gary A. Schultz, Ithaca, NY (US)

(73) Assignee: Advion Biosciences, Inc., Ithaca, NY (US)

( * ) Notice: Subject to any disclaimer, the term of this patent is extended or adjusted under 35 U.S.C. 154(b) by 0 days.

(21) Appl. No.: 10/246,150

(22) Filed: Sep. 17, 2002

(65) Prior Publication Data

US 2003/0057506 A1 Mar. 27, 2003

Related U.S. Application Data (60) Provisional application No. 60/322,862, filed on Sep. 17, 2001.

(51) Int. Cl.[7] ............................. H01J 49/04; H01L 29/76
(52) U.S. Cl. ..................... 250/286; 250/288; 250/281
(58) Field of Search .............................. 250/286, 288, 250/281; 257/411, 142, 520, 649; 438/592

(56) References Cited

U.S. PATENT DOCUMENTS

| | | | | |
|---|---|---|---|---|
| 3,765,935 A | * | 10/1973 | Rand et al. ................. | 257/632 |
| 4,717,631 A | * | 1/1988 | Kaganowicz et al. ...... | 148/33.3 |
| 4,965,218 A | * | 10/1990 | Geissberger et al. ........ | 438/182 |
| 5,241,214 A | | 8/1993 | Herbots et al. | |
| 5,332,697 A | * | 7/1994 | Smith et al. ................ | 438/479 |
| 5,528,058 A | | 6/1996 | Pike, Jr. et al. | |
| 5,883,001 A | * | 3/1999 | Jin et al. .................... | 438/624 |
| 6,111,698 A | | 8/2000 | Woodard et al. | |
| 6,130,472 A | * | 10/2000 | Feger et al. ................ | 257/643 |
| 6,210,986 B1 | * | 4/2001 | Arnold et al. ............... | 438/42 |
| 6,261,934 B1 | | 7/2001 | Kraft et al. | |
| 6,472,076 B1 | * | 10/2002 | Hacker ....................... | 428/447 |
| 6,602,806 B1 | * | 8/2003 | Xia et al. ................... | 438/786 |
| 6,627,882 B2 | * | 9/2003 | Schultz et al. .............. | 250/288 |
| 2003/0030057 A1 | * | 2/2003 | Bencher et al. .............. | 257/77 |

* cited by examiner

Primary Examiner—John R. Lee
Assistant Examiner—Anthony Quash
(74) Attorney, Agent, or Firm—Nixon Peabody LLP

(57) ABSTRACT

A dielectric film is provided which includes a base layer and a capping layer, preferably silicon oxynitride, wherein the film is an effective moisture and ion barrier when disposed between a conductive substrate and a liquid having an electrical potential different than the electrical potential of the substrate.

60 Claims, 3 Drawing Sheets

▲: tested with metal contact electrode on silicon nitride film.
■: tested with liquid electrode on silicon nitride film.

▲: tested with metal contact electrode on silicon nitride film.
■: tested with liquid electrode on silicon nitride film.

Figure 1

▲: tested with metal contact electrode on the silicon nitride film.

■: tested with liquid electrode on silicon nitride film.

Figure 2

▲ : after 100nm silicon oxynitride (SiOxNy) coating of the capping layer;

■ : before 100nm silicon oxynitride coating.

Figure 3

DIELECTRIC FILM

This application claims the benefit of U.S. Provisional Patent Application Ser. No. 60/322,862, filed Sep. 17, 2001, which is herein incorporated by reference in its entirety.

FIELD OF THE INVENTION

The invention relates to a dielectric film and its use as a coating and insulation layer for liquids on electrically conductive materials. In particular, the invention relates to dielectric film and its use as a coating and insulating layer of a device, including microfluidic devices requiring electrical insulation and electrospray devices.

BACKGROUND OF THE INVENTION

The area of miniaturized microfluidic technology, also known as "lab-on-a-chip" or "micro total analysis systems", is rapidly expanding with the promise of revolutionizing chemical analysis and offering enabling tools and technologies for the life sciences. The majority of molecules and compounds of interest in the life sciences are in the liquid phase and typically analytical measurements are used to conduct quantitative and qualitative trace analysis of these analytes in solution. However, due to the nature and origin of the materials under analysis, sample amounts and volumes are historically in short supply and these amounts are constantly decreasing. Moreover, as seen in drug discovery and drug development, including pharmacokinetic and proteomics applications, the need for better analytical measurements that require smaller amounts and volumes of sample is growing. Inherently, microfluidics are a "good fit" for the move to both smaller sample and volume requirements. In fact, a primary reason for miniaturization has been to enhance analytical performance of the device rather than reduce its physical size. Additionally, the ability to miniaturize the analysis with the use of microfluidics allows for integration of multiple separation techniques that enable parallel processing and also for the incorporation of several types of analytical measurements in a single device (sample handling, injections, 2D separations, reaction chambers etc.). Inherently, there are other benefits that accompany miniaturization, such as reduction in reagent and waste disposal, as well as, the reduction of the device footprint.

The first analytical miniaturized device was a gas chromatograph fabricated in silicon over 25 years ago. This device was designed for separating components in the gas phase. A decade later, components of a liquid chromatography column were fabricated on a silicon chip. Most early work related to miniaturization on silicon and the research focused on the fabrication of components such as microvalves, micropumps, and chemical sensors. None of the early systems implemented integrated electronics or electric fields for operation, but rather the silicon was used as a substrate for micromachining desired shapes/geometry.

Most methods used in microfabrication were developed in the 1970's and 1980's in the silicon microprocessor industry. Typically, initial research developments were fabricated in silicon because of the extensive knowledge and tools available for silicon processing. This approach works satisfactorily for devices used for "dry" analyses, however, many microfluidic devices require the integration of on-chip electronics and/or the ability to apply electric fields to device. Because most applications in the life sciences involve samples contained in the liquid phase, the majority of micro analysis systems being developed/designed are for analysis of analytes contained in solution. The need for the ability to apply electric fields to the device becomes a serious issue when processing samples contained in the liquid phase on silicon substrates.

A difficult scenario is encountered due to the opposing objectives of the micro total analysis system and the microprocessor technology used to make them. Typically, the microprocessor industry strives to keep microdevices "dry" and "clean" as liquids, moisture, and contaminates interfere with the device performance and operation. This highly contrasts the needs of micro total analysis systems where liquids and foreign substances (analytes, including salts) are deliberately introduced to the device. Again, this does not pose a problem for a silicon device that does not involve electronic or electrical field generation where only specific geometries are micromachined. However, major issues arise when electronics are incorporated in the devices and especially when potentials are applied for the generation of electric fields (semiconductor must be insulated for controlled electric field generation).

There is currently a move to perform chemical separations on-chip with the use of electric fields, for example applications such as CE, CEC, charged analyte manipulation, and charged solution manipulation. Because of the relatively strong fields needed for the separation process, research has moved to considering non-conductive substrates such as glass, quartz, and non-conducting polymers as opposed to the use of silicon as in the manufacture of semiconductors. This shift in materials is warranted because in order to form the electric fields, the substrates must be insulated in the desired areas.

Although there are conventional techniques for insulating silicon substrates, the dielectric coatings currently available are designed for the electronics industry and operate under "dry" conditions. Much effort in the microprocessor industry has been expended on keeping devices dry or isolated from liquids. Additionally, the microprocessor industry has gone to great lengths to avoid contact of the electronic device with mobile ions such as salts due to the destructive nature they pose to dielectric coatings used to insulate the silicon used in microprocessors.

Microfluidic devices requiring the application of relatively high voltages and electric fields for the manipulation of liquids and samples are mainly fabricated on insulating substrates because of their insulating properties. Application of high voltages to liquids on insulators on conductor substrates often leads to shorting or drastically reduced performance and lifetime of desired electrical properties.

Accordingly, the art needs dielectric coatings that do not degrade, but rather maintain their electrical properties when exposed to direct voltage application and high electric field strengths while in the presence of high humidity and/or direct liquid contact (wet). The art needs to overcome current coating technology limitations and provide appropriate solutions for microfluidic device applications. The art needs microfluidic devices that take advantage of the highly developed silicon processing techniques for silicon and other substrates including micromachining as well as electronic circuit integration and electric field definition. The art lacks the ability to incorporate microfluidics and electronics in the same substrate allowing for fully integrated systems.

SUMMARY OF THE INVENTION

One aspect of the present invention relates to a dielectric film including a base layer and a capping layer, wherein the film is an effective moisture and ion barrier when disposed between a conductive substrate and a liquid having an electrical potential different than the electrical potential of the substrate.

Another aspect of the present invention relates to a device including a conductive substrate, at least a portion thereof coated with a dielectric layer including a base layer and a capping layer and a liquid in contact with the dielectric layer.

Another aspect of the present invention relates to a method for preventing the migration of ions from a solution to a conductive substrate having an electrical potential different than that of the solution, including providing a dielectric film layer including a base layer and an oxynitride capping layer interposed between the substrate and the solution The present invention results in a number of advantages over the prior art. It is an advantage of the present invention to provide a dielectric coating that does not degrade and maintains its electrical properties when exposed to direct voltage application and high electric field strengths while in the presence of high humidity and/or direct liquid contact (wet). The invention overcomes current coating technology limitations and provides appropriate solutions to microfluidic device applications. This invention allows microfluidic devices to take advantage of the highly developed silicon processing techniques for silicon and other substrates including micromachining as well as electronic circuit integration and electric field definition. Microfluidics and electronics may now be made in the same substrate allowing for fully integrated systems.

Other advantages of the present invention will be apparent to those skilled in the art from the following description and the appended claims.

DETAILED DESCRIPTION OF THE INVENTION

The present invention relates to a dielectric film that maintains its electrical properties when exposed to a direct voltage application and high electric field strength while in the presence of high humidity and/or direct liquid contact.

The dielectric film of the present invention is a multiple layer barrier which prevents penetration of moisture and ions from a liquid into a substrate when an electrical potential difference is applied between the liquid and a conductive portion of the substrate. The dielectric film is suitable for use on any microfluidic device which requires that an electrical potential difference is generated between a conductive substrate and a fluid. Suitable uses of the barrier layer of the present invention include use in separation devices using electric fields, such as, capillary electrophoresis and capillary electrochromatography; microfluidic devices; electrospray devices including those disclosed in or fabricated in accordance with U.S. patent application Ser. No. 09/468,53 5, filed Dec. 20, 1999, entitled "Integrated Monolithic Microfabricated Dispensing Nozzle and Liquid Chromatography-Electrospray System and Method" to Schultz et al., and U.S. patent application Ser. No. 09/748, 518, filed Dec. 22, 2000, entitled "Multiple Electrospray Device, Systems and Methods" to Schultz et al., which are herein incorporated by reference in their entirety; liquid chromatography devices; liquid chromatography/electrospray devices; electrostatic actuation on a silicon device; droplet dispensing using electric fields for a device on silicon or conductor; silicon-based fuel injectors; and the like.

Suitable devices include those having critical or limiting features of from about 0.1 microns to about 1 mm.

The dielectric layer of the present invention is particularly suited for use in devices for electrospray ionization which provides for the atmospheric pressure ionization of a liquid sample. The electrospray process creates highly-charged droplets that, under evaporation, create ions representative of the species contained in the solution. An ion-sampling orifice of a mass spectrometer may be used to sample these gas phase ions for mass analysis. When a positive voltage is applied to the tip of the capillary relative to an extracting electrode, such as one provided at the ion-sampling orifice of a mass spectrometer, the electric field causes positively-charged ions in the fluid to migrate to the surface of the fluid at the tip of the capillary. When a negative voltage is applied to the tip of the capillary relative to an extracting electrode, such as one provided at the ion-sampling orifice to the mass spectrometer, the electric field causes negatively-charged ions in the fluid to migrate to the surface of the fluid at the tip of the capillary.

When the repulsion force of the solvated ions exceeds the surface tension of the fluid being electrosprayed, a volume of the fluid is pulled into the shape of a cone, known as a Taylor cone, which extends from the tip of the capillary. A liquid jet extends from the tip of the Taylor cone and becomes unstable and generates charged-droplets. These small charged droplets are drawn toward the extracting electrode. The small droplets are highly-charged and solvent evaporation from the droplets results in the excess charge in the droplet residing on the analyte molecules in the electrosprayed fluid. The charged molecules or ions are drawn through the ion-sampling orifice of the mass spectrometer for mass analysis. This phenomenon has been described, for example, by Dole et al., Chem. Phys. 49:2240 (1968) and Yamashita et al., J. Phys. Chem. 88:4451 (1984). The potential voltage ("V") required to initiate an electrospray is dependent on the surface tension of the solution as described by, for example, Smith, IEEE Trans. Ind. Appl. 1986, IA-22:527–35 (1986). Typically, the electric field is on the order of approximately $10^6$ V/m. The physical size of the capillary and the fluid surface tension determines the density of electric field lines necessary to initiate electrospray.

When the repulsion force of the solvated ions is not sufficient to overcome the surface tension of the fluid exiting the tip of the capillary, large poorly charged droplets are formed. Fluid droplets are produced when the electrical potential difference applied between a conductive or partly conductive fluid exiting a capillary and an electrode is not sufficient to overcome the fluid surface tension to form a Taylor cone.

*Electrospray Ionization Mass Spectrometry: Fundamentals, Instrumentation, and Applications,* edited by R. B. Cole, ISBN 0-471-14564-5, John Wiley & Sons, Inc., New York summarizes much of the fundamental studies of electrospray. Several mathematical models have been generated to explain the principals governing electrospray. Equation 1 defines the electric field $E_c$ at the tip of a capillary of radius $r_c$ with an applied voltage $V_c$ at a distance $d$ from a counter electrode held at ground potential:

$$E_c = \frac{2V_c}{r_c \ln(4d/r_c)} \quad (1)$$

The electric field $E_{on}$ required for the formation of a Taylor cone and liquid jet of a fluid flowing to the tip of this capillary is approximated as:

$$E_{on} \approx \left(\frac{2\gamma\cos\theta}{\varepsilon_o r_c}\right)^{1/2} \quad (2)$$

where $\gamma$ is the surface tension of the fluid, $\theta$ is the half-angle of the Taylor cone and $\epsilon_0$ is the permittivity of vacuum. Equation 3 is derived by combining equations 1 and 2 and approximates the onset voltage $V_{on}$ required to initiate an electrospray of a fluid from a capillary:

$$V_{on} \approx \left(\frac{r_c \gamma \cos\theta}{2\varepsilon_0}\right)^{1/2} \ln(4d/r_c) \quad (3)$$

As can be seen by examination of equation 3, the required onset voltage is more dependent on the capillary radius than the distance from the counter-electrode.

The electrospray device forms a stable electrospray of all fluids commonly used in CE, CEC, and LC. The surface tension of solvents commonly used as the mobile phase for these separations range from 100% aqueous ($\gamma$=0.073 N/m) to 100% methanol ($\gamma$=0.0226 N/m). As the surface tension of the electrospray fluid increases, a higher onset voltage is required to initiate an electrospray for a fixed capillary diameter. As an example, a capillary with a tip diameter of 14 $\mu$m is required to electrospray 100% aqueous solutions with an onset voltage of 1000 V. The work of M. S. Wilm et al., *Int. J. Mass Spectrom. Ion Processes* 136:167–80 (1994), first demonstrates nanoelectrospray from a fused-silica capillary pulled to an outer diameter of 5 $\mu$m at a flow rate of 25 nL/min. Specifically, a nanoelectrospray at 25 nL/min was achieved from a 2 $\mu$m inner diameter and 5 $\mu$m outer diameter pulled fused-silica capillary with 600–700 V at a distance of 1–2 mm from the ion-sampling orifice of an electrospray equipped mass spectrometer.

Electrospray in front of an ion-sampling orifice of an API mass spectrometer produces a quantitative response from the mass spectrometer detector due to the analyte molecules present in the liquid flowing from the capillary. One advantage of electrospray is that the response for an analyte measured by the mass spectrometer detector is dependent on the concentration of the analyte in the fluid and independent of the fluid flow rate. The response of an analyte in solution at a given concentration would be comparable using electrospray combined with mass spectrometry at a flow rate of 100 $\mu$L/min compared to a flow rate of 100 nL/min. D. C. Gale et al., *Rapid Commun. Mass Spectrom.* 7:1017 (1993) demonstrate that higher electrospray sensitivity is achieved at lower flow rates due to increased analyte ionization efficiency. Thus by performing electrospray on a fluid at flow rates in the nanoliter per minute range provides the best sensitivity for an analyte contained within the fluid when combined with mass spectrometry.

Thus, it is desirable to integrate an electrospray device of microchip-based separation devices with API-MS instruments. This integration places a restriction on the capillary tip defining a nozzle on a microchip. This nozzle will, in all embodiments, exist in a planar or near planar geometry with respect to the substrate defining the separation device and/or the electrospray device. When this co-planar or near planar geometry exists, the electric field lines emanating from the tip of the nozzle will not be enhanced if the electric field around the nozzle is not defined and controlled and, therefore, an electrospray is only achievable with the application of relatively high voltages applied to the fluid.

The dielectric layer of the present invention is particularly well suited for use in such electrospray devices which require the application of relatively high voltages applied to the fluid. We have discovered that the conventional dielectric films used in microelectronics under the standard "dry" conditions do not behave similarly under high moisture and/or "wet" conditions as occurs with the contact of liquids in microfluidic devices. Additionally, the behavior of conventional dielectric films used in microelectronics under the standard "dry" conditions is not similar to their behavior in high electric filed strengths under high moisture and/or wet conditions.

The dielectric films of the present invention enable establishing and maintaining an electric field for a prolonged period of time while insulating the liquid from the conductive parts of the device. We discovered that the electric characteristics of conventional dielectric films change when contacted by liquid electrodes or liquids at different potentials than the conductive regions of the device. The present invention prevents deterioration of the performance of a microfluidic device during prolonged sampling. This invention recognizes the mechanism behind the deterioration and provides coating solutions appropriate to microfluidic device applications.

The dielectric coatings of the present invention do not loose their insulating properties when exposed/contacted to high voltage carrying liquids for extended periods of time. The dielectric film of the present invention provides a barrier to moisture and ionic species when exposed to a high field strengths. The barrier is maintained for at least 30 seconds and can last hours, days, years and longer.

The dielectric film of the present invention includes at least a base layer and a capping layer. The base layer includes any conventional insulation material. The capping layer includes any suitable condensed film layer.

Silicon nitride has long been known as a material of high dielectric strength, moisture and ion diffusion barrier, and having chemical inertness. It would therefore seem likely as a good candidate for use in microfluidic device applications. We discovered that silicon nitride in contact with fluid is a good moisture and ion diffusion barrier when there is no electric field present. However, when voltages are applied to a liquid in contact with a silicon nitride film, its dielectric strength deteriorates to an extent depending on the composition and the preparation method of the silicon nitride. It is therefore desirable to improve the barrier properties to provide a more robust dielectric layer that can withstand higher voltages for longer periods of time.

Figure 1:
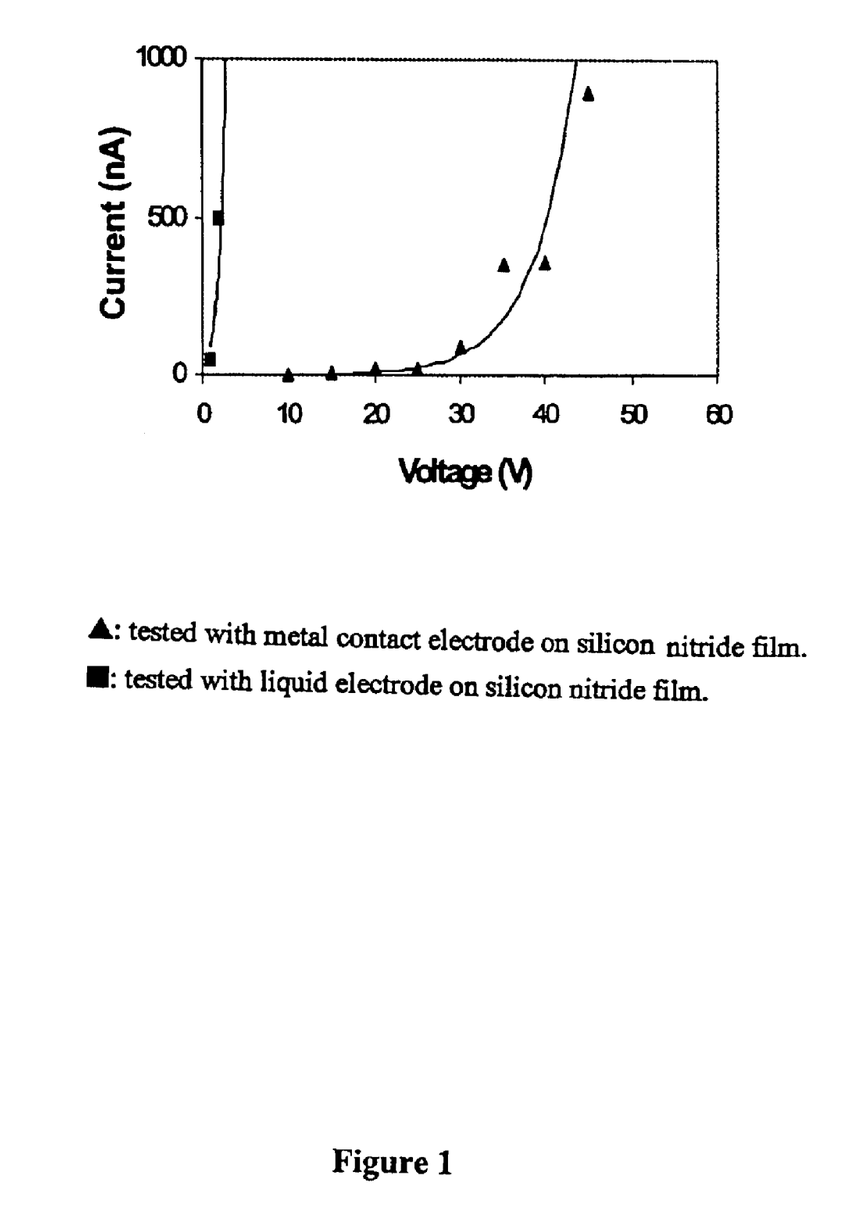
FIG. 1 is a graph of the current/voltage characteristics of a 100 nm thick low stress silicon nitride film on a silicon substrate.

FIG. 1 shows the I–V characteristics of 100 nm thick low stress silicon nitride film. A significant deterioration in dielectric strength is seen when liquid is used to make electrical contact with the silicon nitride surface. It was discovered that a thin (several hundred angstroms) condensed film on the surface of the silicon nitride layer surprisingly improves the dielectric strength of the coating when a difference in potential is applied with a liquid electrode.

The term "condensed film" is defined in the context of the present invention as a highly dense coating with a very limited porous structure and not granular in nature. Suitable materials for the condensed film layer include high stress silicon nitride; oxy nitride; diamond like carbon; and the like.

While not being bound by any theory, we believe that the deterioration observed results from the ions and molecules in the liquid being driven into the film through nano-porous structures. The chemical vapor deposition (CVD) low stress silicon nitride film commonly used in microelectronics as an ion and moisture barrier can be improved in dielectric strength suitable for use in microfluidic device applications by adding a thin layer of the capping film of the present invention.

CVD stoichiometric silicon nitride is of high dielectric strength and is a condensed material. However, stress in the film may result from the high thermal expansion coefficient difference between that of the silicon substrate and the silicon nitride layer. We discovered that nano-cracking can occur in the film long before pealing occurs when going through processes of elevated temperature or just in growing the thickness of the film. These micro-cracks do not affect the dielectric strength of the film when contacted with a metal electrode (dry scenario), but they may deteriorate the dielectric strength of the film when electric contact is made with a liquid.

Figure 2:
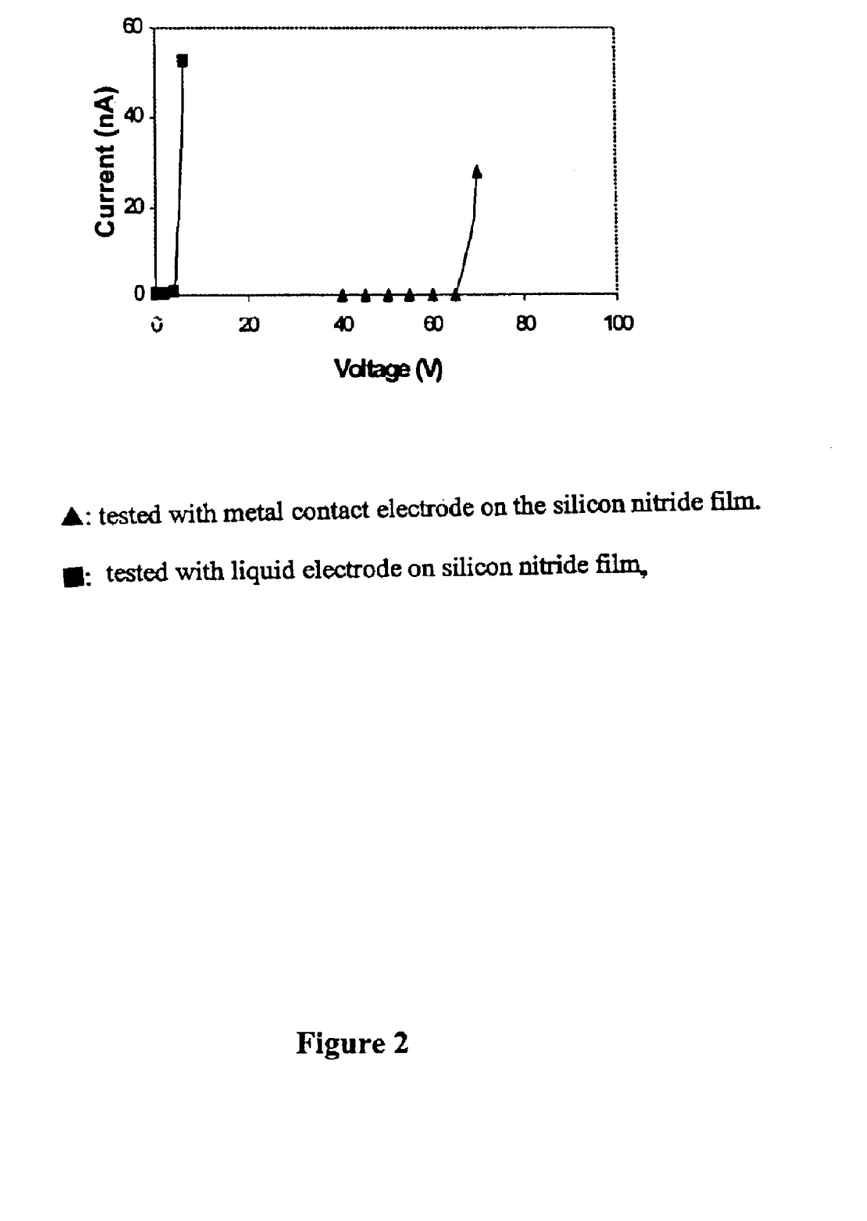
FIG. 2 is a graph of the current/voltage characteristics of a 100 nm thick high stress silicon nitride film on a silicon substrate.

FIG. 2 shows the I–V characteristics of 100 nm thick high stress silicon nitride film with different contacting electrodes. The film was deposited with low pressure chemical vapor deposition ("LPCVD") and an 1100° C. annealing step was added following the deposition. An optical microscope of up to 1000× magnification and a SEM have been used to examine the film surface. No cracks or pealing were observed. However, one can see the significant difference between the two I–V curves in FIG. 2. The dielectric strength of the film has significantly deteriorated where the potential is applied with a liquid electrode to the extent that the film has almost become a conductor. This indicates that the film has developed nanometer size cracks. This leads to a conclusion that while a condensed and stressed dielectric film can be used successfully in microelectronic devices, such films may cause failure and be unsuitable for use in microfluidic devices.

We discovered that a thin (ten to several hundred nanometers) condensed film deposited conformally on the surface of the low stress silicon nitride can drastically improve the dielectric strength in liquid electric contacts. In electrospray applications, the dielectric film is preferably from about 0.1 micron to about 10 microns thick.

Figure 3:
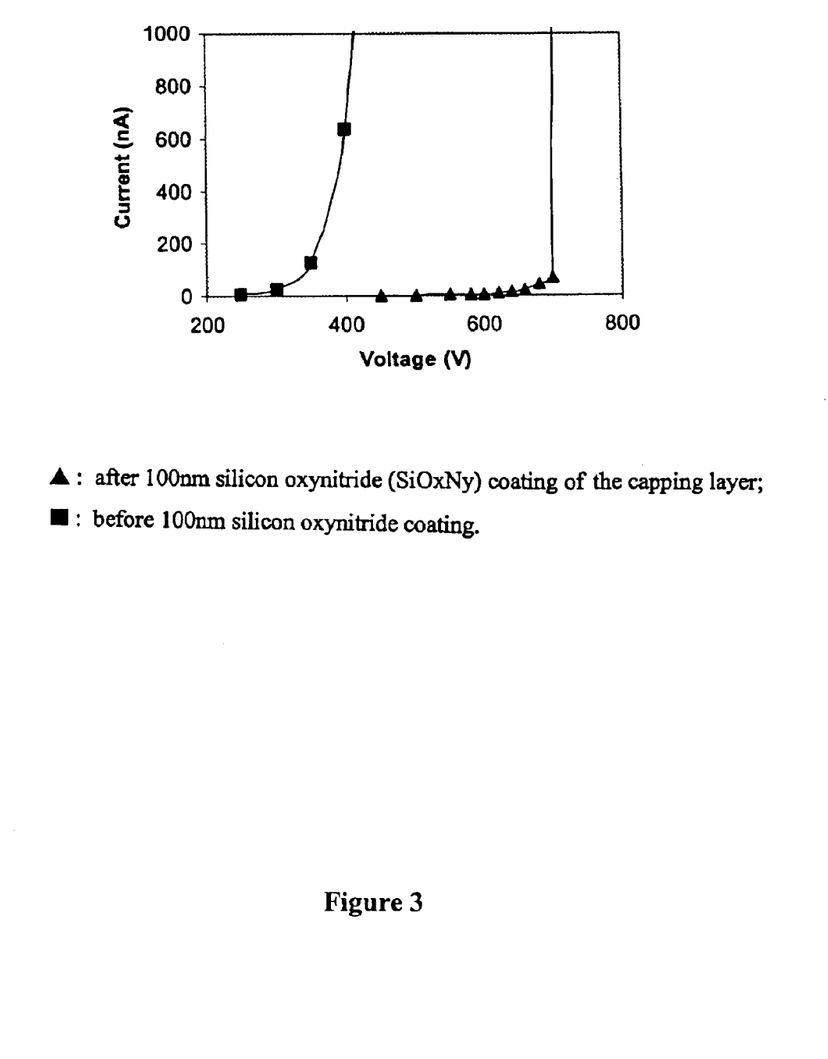
FIG. 3 is a graph of the current/voltage characteristics of 1.5 μm LPCVD low stress silicon nitride film on a silicon substrate with liquid electric contact after a 100 nm silicon oxynitride (SiOxNy) coating and before a 100 nm silicon oxynitride coating.

FIG. 3 shows the current/voltage (I–V) characteristics of 1.5 μm low stress silicon nitride LPCVD on a silicon substrate. I–V curves were measured with liquid electric contact on the film with and without a 100 nm silicon oxynitride capping layer. A review of the results indicates that the dielectric strength of the silicon nitride film is almost doubled by application of the thin capping layer. The dielectric strength of the layer with the capping layer when in contact with the liquid is close to that of the dielectric strength of the layer without the capping layer when a dry electric contact is used. The thin capping layer prevents the deterioration of low stress silicon nitride resulting from electric contact with a liquid.

In a microfluidic device fabricated on a silicon wafer, a combination of thermal silicon oxide plus low stress LPCVD silicon nitride plus a thin silicon oxynitride capping layer results in a high quality performance in terms of dielectric strength with liquid electric contact. We have achieved about a 3000 volt breakdown voltage on mnicrofluidic electrospray nozzle devices in liquid with a combination coating of 2.5 μm thermal oxide +1.5 μm low stress silicon nitride +300 nm silicon oxynitride. Further, a dielectric layer composed of about 3 μm thermal oxide +about 2 μm low stress silicon nitride +1 pm silicon oxynitride would be expected to withstand up to about 4300 volts. In another embodiment, the dielectric layer has a base layer of 2.5 μm film of oxide and a capping layer of 1 μm film of silicon. The dielectric layers of the present invention are capable of withstanding voltages of up to about 5000 volts, preferably between about 1200 V to about 5000 V and maintaining dielectric and ion barrier properties in a liquid environment for an infinite period of time. The dielectric layers of the present invention are capable of withstanding voltages up to about 1200 volts for an infinite time.

The thin capping layer on low stress nitride is not limited to silicon oxynitride. It can be any other condensed dielectric material. It can be stressed film as well since its small thickness will not result in any film cracking.

Suitable materials for the base layer include but are not limited to: silicon oxide based materials, silicon dioxide based dielectric film including silicon dioxide ($SiO_2$), off-stoichiometric silicon dioxide and doped silicon dioxide; silicon nitride based dielectric film including silicon nitride ($Si_3N_4$), off-stoichiometric silicon nitride and doped silicon nitride; silicon nitride having a Refractive Index of from about 2.1 to about 3, preferably about 2.1 to about 2.3; ceramic based dielectric materials; transition metal oxide based dielectric materials; and the like.

Suitable materials for the capping layer include but are not limited to: condensed film; silicon oxynitride ($SiO_xN_y$); off-stoichiometric silicon oxynitride; hydrogen-comprised silicon oxynitride ($SiO_xN_yH_z$); doped silicon oxynitrides; oxynitride having a Refractive Index from about 1.4 to about 2, preferably about 1.6 to about 1.8; silicon nitride ($Si_3N_4$) having a Refractive Index of from about 2 to about 2.09; Diamond Like Carbon (DLC); ceramic based dielectric materials; transition metal oxide based dielectric materials; and the like.

The capping layer deposition methods include but are not limited to: (1) LPCVD and other CVDs; (2) Physical Vapor Deposition (PVD); (3) thermal oxidation of amorphous or poly-silicon or silicon compounds.

We discovered experimentally that for a microfluidic device, especially in an electrospray ionization nozzle application, the dielectric surface coating of the present invention possess the following properties: (1) high dielectric strength which allows for the application to liquids of high electric voltages; (2) low or zero mechanical stress in the coated films; (3) conformal coating (uniform film thickness over the entire surface of the device) and smooth film surface; (4) condensed materials without any porous structures; (5) moisture barrier; (6) resistance to ion diffusion; (7) chemically inert; (8) controllable chemical surfaces (hydrophobic or hydrophilic surfaces). The dielectric layer of the present invention is capable of forming an insulation layer under a plethora of different solvent compositions ranging from 100% aqueous to 100 % organic solutions or a mix thereof including all solvent compositions used in modern liquid chromatography and separation systems. These solvents also contain high concentrations of ionic species, salts, and small and large drug molecules. The liquid electrode used for the following examples was composed of 50% water, 50 alcohol, with approximately 1% acid.

Examples 1–3 generate data showing the specific breakdown for single/isolated films indicating the difference in performance under dry vs. wet conditions. In order to achieve higher applied potentials and stronger electric fields a combination of various different films may be desired. It should be noted that there are fundamental thickness limitations of a given film because of the inherent stresses generated during growth of the film. The combination of varying thin film layers yields the ability to apply higher voltages and higher field strength under wet conditions. Using various materials, "stacks", allows the ability to take advantage of various positive attributes of a specific coating when combined with other coatings for an overall greater performance. In addition, by alternating the thin film stack in a repeatable fashion, film stress issues may be relieved or reduced allowing for an overall thicker layer to be formed.

An example of silicon coated with a conformal thin film stack yields a device capable of withstanding applied voltages of several kilovolts or more under wet conditions. Prior to this invention, there is no film technology, conformal in nature, capable of allowing such high voltage to be applied to microfluidic devices.

The following examples illustrate several embodiments of the present invention. However, the invention should not be limited to the embodiments illustrated.

EXAMPLE 1

Data for FIG. 1 was generated using the following experimental setup and conditions. A silicon wafer was cleaned using semiconductor cleaning protocols (MOS clean). 100 nm low stress nitride was deposited on a silicon wafer in a low-pressure chemical vapor deposition oven. The sample was then cleaved and placed in an electrical test apparatus for assessment of the dielectric breakdown strength of the thin film. Conductive epoxy was used to make good electrical contact between the silicon substrate (cleaved edge of the wafer) and the grounded metal stage. Positive (or negative) voltage was applied under dry conditions using a metal electrode, or under wet conditions, utilizing a fluid electrode. The voltage was ramped up in a stepwise fashion while simultaneously monitoring the current leaking through the film to the silicon substrate. The curve was recorded and the data can be seen in FIG. 1. It is seen from this data that the current—voltage characteristics of the low stress silicon nitride film is significantly different in the dry (metal electrode) as compared to the wet (liquid electrode) scenario with a much lower dielectric strength of the film for the liquid electric contact example.

EXAMPLE 2

Data for FIG. 2 was generated using the following experimental setup and conditions. A silicon wafer was cleaned using semiconductor cleaning protocols (MOS clean). 100nm of high stress nitride was deposited on a silicon wafer in a low-pressure chemical vapor deposition oven. The sample was then cleaved and placed in an electrical test apparatus for assessment of the dielectric breakdown strength of the thin film. Conductive epoxy was used to make good electrical contact between the silicon substrate (cleaved edge of the wafer) and the grounded metal stage. Positive (or negative) voltage was applied under dry conditions using a metal electrode, or under wet conditions, utilizing a fluid electrode. The voltage was ramped up in a stepwise fashion while simultaneously monitoring the current leaking through the film to the silicon substrate. The curve was recorded and the data can be seen in FIG. 2. It is seen from this data that the nitride film has much less dielectric strength in the liquid (wet) electric contact than in the metal (dry) electrical contact. There was no such difference before annealing. This data implies that nano-scale cracking has been produced in the film due to stress. Current—voltage characteristics of the high stress silicon nitride film is significantly different in the dry (metal electrode) as compared to the wet (liquid electrode) scenario with a much lower dielectric strength of the film for the liquid electric contact example.

EXAMPLE 3

Data for FIG. 3 was generated using the following experimental setup and conditions. A silicon wafer was cleaned using semiconductor cleaning protocols (MOS clean). 1.5 $\mu$m of low stress nitride was deposited on a silicon wafer in a low-pressure chemical vapor deposition oven. The wafer was then cleaved and one pieces was preserved for electrical testing with only the low stress nitride and another piece was further processed with the addition of a subsequent deposition of 100 nm of oxynitride. The samples were then cleaved and placed in an electrical test apparatus for assessment of the dielectric breakdown strength of the thin film. Conductive epoxy was used to make good electrical contact between the silicon substrates (cleaved edges of the wafer) and the grounded metal stage. Positive (or negative) voltage was applied under dry conditions using a metal electrode, or under wet conditions, utilizing a fluid electrode for both samples. The voltage was ramped up in a stepwise fashion while simultaneously monitoring the current leaking through the film to the silicon substrate. The curves were recorded and the data can be seen in FIG. 3. After the coating of the oxynitride capping significant improvement is seen in the dielectric strength of the film in contact with the liquid electrode. The dielectric strength has been enhanced by greater than 100%.

EXAMPLE 4

A silicon electrospray device having a dielectric film stack of oxide/Low Stress nitride/oxynitride is prepared according to the following procedure.

This example provides a dielectric stack of oxynitride on low stress nitride on oxide on a silicon substrate.

Growth of Silicon Dioxide

The silicon substrate is cleaned and prepared for the thermal oxidation of the silicon for growth of 2.5 $\mu$m silicon dioxide. The growing of the silicon dioxide layer is conducted in an atmospheric furnace using a steam oxide with the furnace being held at approximately ~1100–1200° C. After growth of the film, an anneal step is conducted in a nitrogen atmosphere.

Deposition of Low Stress Nitride

After growth of the silicon dioxide, the substrate is transferred to a low pressure chemical vapor deposition furnace for deposition of approximately 1.5 $\mu$m of low stress nitride. The furnace gases for the low stress nitride deposition include dichlorosilane and $NH_3$. Furnace conditions include a temperature and pressure of approximately 800–900° C. and 300 mtorr, respectively. The Refractive Index of the low stress nitride is approximately 2.2.

Deposition of Oxynitride

After depositing the low stress nitride, 0.3 $\mu$m oxynitride is deposited (in the same or a different furnace) in a low-pressure chemical vapor deposition furnace. Furnaces gases include $NH_3$, $N_2O$, and silane (or dichlorosilane). Furnace conditions include a temperature and pressure of approximately 800–900° C. and 260 mtorr, respectively. The Refractive Index of the oxynitride is approximately 1.71.

The dielectric strength of the combined stack held greater than 3000 volts under wet conditions.

Some variation of the above conditions may be conducted for the desired out come. In addition to the low-pressure process listed above, various methods for employing the film application may be conducted, such as plasma enhanced chemical vapor deposition.

What is claimed is:

1. A dielectric film comprising:
    a first layer of an electrically insulating material conformally covering all liquid-contacting portions of an electrically conductive microfluidic substrate having at least one feature within the range of from about 0.1 microns to about 1 mm in size; and
    a second layer, wherein the second layer is a condensed film deposited conformally on at least all liquid-contacting portions of the first layer; and
    wherein said first layer is a 25 $\mu$m film of oxide to which an intermediate layer of a 1.5 $\mu$m film of nitride is added and the second layer is a 0.3 $\mu$m film of silicon oxynitride; and
    wherein the dielectric film is from about 0.1 to about 10 microns thick and is an effective moisture and ion barrier when disposed between said substrate and a liquid having an electrical potential different than the electrical potential of said substrate.

2. The dielectric film of claim 1, wherein said dielectric film has a dielectric strength of from 200 to 716 volts per micron.

3. The dielectric film of claim 1, wherein said second layer comprises silicon oxynitride; off-stoichiometric silicon oxynitride; hydrogen-comprised silicon oxynitride; doped silicon oxynitride; oxynitride having a Refractive Index of from about 1.4 to about 2; silicon nitride having a Refractive Index of from about 2 to about 2.09; Diamond Like Carbon; ceramic based dielectric materials; or transition metal oxide based dielectric materials.

4. The dielectric film of claim 1, wherein said first layer comprises silicon oxide based materials, silicon dioxide based dielectric film; silicon dioxide; off-stoichiometric silicon dioxide; doped silicon dioxide; silicon nitride based dielectric film; silicon nitride; off-stoichiometric silicon nitride; doped silicon nitride; silicon nitride having a Refractive Index of from about 2.1 to about 3; ceramic based dielectric materials; or transition metal oxide based dielectric materials.

5. The dielectric film of claim 1, wherein said dielectric film is an effective moisture and ion barrier when the electrical potential difference between the conductive substrate and the liquid is from about 1200 volts to about 5000 volts.

6. The dielectric film of claim 5, wherein said dielectric film is an effective moisture and ion barrier when the electrical potential difference between the conductive substrate and the liquid is about 4300 volts.

7. The dielectric film of claim 5, wherein said dielectric film is an effective moisture and ion barrier when the electrical potential difference between the conductive substrate and the liquid is about 1200 volts.

8. The dielectric film of claim 1, wherein said second layer comprises silicon oxynitride having a Refractive Index from about 1.6 to about 1.8.

9. The dielectric film of claim 1, wherein said first layer is a 2.5 $\mu$m film of oxide and the second layer is a 1 $\mu$m film of silicon oxynitride.

10. The dielectric film of claim 1, wherein the second layer is three-hundred angstroms or less thick.

11. The dielectric film of claim 1, wherein the second layer is several hundred angstroms thick.

12. The dielectric film of claim 1, wherein the second layer is from ten to three hundred nanometers thick.

13. The dielectric film of claim 1, wherein the second layer is 1 $\mu$m or less thick.

14. The dielectric film of claim 1, wherein said dielectric film is an effective moisture and ion barrier when the electrical potential difference between the conductive substrate and the liquid is maintained for at least 30 seconds.

15. The dielectric film of claim 1, wherein said liquid contains at least one ionic species.

16. A device comprising:
    an electrically conductive substrate;
    a condensed dielectric film comprising a first layer of electrically insulating material and a second layer, the dielectric film deposited conformally on at least all liquid-contacting portions of the substrate;
    an electrically conductive liquid in contact with the dielectric film; and
    a voltage applied to the device such that there is an electrical potential difference between the liquid and the substrate and wherein said first layer is a 2.5 $\mu$m film of oxide to which an intermediate layer of a 1.5 $\mu$m film of nitride is added and the second layer is a 0.3 $\mu$m film of silicon oxynitride; and wherein the dielectric film is from about 0.1 to about 10 microns thick and is an effective moisture and ion barrier when disposed between said substrate and a liquid having an electrical potential different than the electrical potential of said substrate.

17. The device of claim 16, wherein said device is an electrospray device, liquid chromatography device, combination liquid chromatography/electrospray device, capillary electrophoresis, capillary electrochromatography, combination capillary electrophoresis/electrospray device, combination capillary electrochromatography/electrospray device, electrostatic actuation on a silicon device, droplet dispensing device on a conductor using electric fields, or silicon based fuel injector.

18. The device of claim 16, wherein said dielectric film has a dielectric strength of from 200 to 716 volts per micron.

19. The device of claim 16, wherein said second layer comprises silicon oxynitride; off-stoichiometric silicon oxynitride; hydrogen-comprised silicon oxynitride; doped silicon oxynitride; oxynitride having a Refractive Index of from about 1.4 to about 2; silicon nitride having a Refractive Index of from about 2 to about 2.09; Diamond Like Carbon; ceramic based dielectric materials; or transition metal oxide based dielectric materials.

20. The device of claim 16, wherein said first layer comprises silicon oxide based materials, silicon dioxide based dielectric film; silicon dioxide; off-stoichiometric silicon dioxide; doped silicon dioxide; silicon nitride based dielectric film; silicon nitride; off-stoichiometric silicon nitride; doped silicon nitride; silicon nitride having a Refractive Index of from about 2.1 to about 3; ceramic based dielectric materials; or transition metal oxide based dielectric materials.

21. The device of claim 16, wherein said dielectric film is an effective moisture and ion barrier when the electrical potential difference between the conductive substrate and the liquid is from about 1200 volts to about 5000 volts.

22. The device of claim 21, wherein said dielectric film is an effective moisture and ion barrier when the electrical potential difference between the conductive substrate and the liquid is about 4300 volts.

23. The device of claim 21, wherein said dielectric film is an effective moisture and ion barrier when the electrical potential difference between the conductive substrate and the liquid is about 1200 volts.

24. The device of claim 16, wherein said second layer comprises silicon oxynitride having a Refractive Index of from about 1.6 to about 1.8.

25. The device of claim 16, wherein said first layer is a 2.5 µm film of oxide and the second layer is a 1 µm film of silicon oxynitride.

26. The device of claim 16, wherein the second layer is three-hundred angstroms or less thick.

27. The device of claim 16, wherein the second layer is several hundred angstroms thick.

28. The device of claim 16, wherein the second layer is from ten to three hundred nanometers thick.

29. The device of claim 16, wherein the condensed film is 1 µm or less thick.

30. The device of claim 16, wherein the dielectric film is an effective moisture and ion barrier when the electrical potential difference between the conductive substrate and the liquid is maintained for at least 30 seconds.

31. The device of claim 16, wherein the dielectric film is an effective moisture and ion barrier when the liquid contains at least an ionic species.

32. The device of claim 16, wherein the dielectric film is from about 0.1 microns to about 10 microns thick.

33. The device of claim 16, wherein the conductive substrate has physical features within the range of from about 0.1 microns to about 1 mm in size.

34. A method for creating an electrical field in a liquid-containing device by preventing electrical current from flowing between a conductive liquid and a conductive microfluidic substrate in contact with the liquid, the method comprising:
  providing a conductive microfluidic substrate having at least one feature within the range of from about 0.1 microns to about 1 mm in size;
  conformally coating at least all liquid-contacting portions of the conductive microfluidic substrate with a condensed dielectric film comprising a first layer and a second layer; and
  wherein said first layer is a 2.5 µm film oxide to which an intermediate layer of a 1.5 µm film of nitride is added and the second layer is a 0.3 µm film of silicon oxynitride; and
  applying a voltage to the device such that there is an electrical potential difference between the liquid and the conductive microfluidic substrate.

35. The method of claim 34, wherein said dielectric film layer has a dielectric strength of from 200 to 716 volts per micron.

36. The method of claim 34, wherein said second layer comprises silicon oxynitride; off-stoichiometric silicon oxynitride; hydrogen-comprised silicon oxynitride; doped silicon oxynitride; oxynitride having a Refractive Index of from about 1.4 to about 2; silicon nitride having a Refractive Index of from about 2 to about 2.09; Diamond Like Carbon; ceramic based dielectric materials; or transition metal oxide based dielectric materials.

37. The method of claim 34, wherein said first layer comprises silicon oxide based materials, silicon dioxide based dielectric film; silicon dioxide; off-stoichiometric silicon dioxide; doped silicon dioxide; silicon nitride based dielectric film; silicon nitride; off-stoichiometric silicon nitride; doped silicon nitride; silicon nitride having a Refractive Index of from about 2.1 to about 3; ceramic based dielectric materials; or transition metal oxide based dielectric materials.

38. The method of claim 34, wherein said dielectric film is an effective moisture and ion barrier when the electrical potential difference between the conductive substrate and the liquid is from about 1200 volts to about 5000 volts.

39. The method of claim 38, wherein said dielectric film is an effective moisture and ion barrier when the electrical potential difference between the conductive substrate and the liquid is about 4300 volts.

40. The method of claim 38, wherein said dielectric film is an effective moisture and ion barrier when the electrical potential difference between the conductive substrate and the liquid is about 1200 volts.

41. The method of claim 34, wherein said second layer comprises silicon oxynitride having a Refractive Index of from about 1.6 to about 1.8.

42. The method of claim 34, wherein said first layer is a 2.5 µm film of oxide and the second layer is a 1 µm film of silicon oxynitride.

43. The method of claim 34, wherein the second layer is three-hundred angstroms or less thick.

44. The method of claim 34, wherein the second layer is from ten to three hundred nanometers thick.

45. The method of claim 34, wherein the condensed film is 1 µm or less thick.

46. The method of claim 34, wherein the second layer is several hundred angstroms thick.

47. The method of claim 34, wherein said dielectric film is an effective moisture and ion barrier when the electrical potential difference between the conductive substrate and the liquid is maintained for at least 30 seconds.

48. The method of claim 34, wherein said liquid contains at least one ionic species.

49. The method of claim 34, wherein the dielectric film is from about 0.1 microns to about 10 microns thick.

50. A method for making a device comprising:
  forming a first layer of a condensed film insulating material conformally on a microfluidic silicon substrate, having at least one feature within the range of from about 0.1 microns to about 1 mm in size;
  vapor depositing a condensed film second layer conformally on the surface of the insulating material such that the condensed film second layer is from about ten nanometers to three hundred nanometers thick, wherein the first layer is a 2.5 µm film of oxide to which an intermediate layer of a 1.5 µm film of nitride is added and the second layer is a 0.3 µm film of silicon oxynitride; and wherein the second layer comprises silicon oxynitride; off-stoichiometric silicon oxynitride; hydrogen-comprised silicon oxynitride; doped silicon oxynitride; oxynitride having a Refractive Index of from about 1.4 to about 2; silicon nitride having a Refractive Index of from about 2 to about 2.09; Diamond Like Carbon; ceramic based dielectric materials; or transition metal oxide based dielectric materials; and
  annealing the condensed film second layer.

51. The method of claim 50, wherein the first layer comprises silicon oxide based materials, silicon dioxide based dielectric film; silicon dioxide; off-stoichiometric silicon dioxide; doped silicon dioxide; silicon nitride based dielectric film; silicon nitride; off-stoichiometric silicon nitride; doped silicon nitride; silicon nitride having a Refractive Index of from about 2.1 to about 3; ceramic based dielectric materials; or transition metal oxide based dielectric materials.

52. The method of claim 50, wherein the device is an effective moisture and ion barrier when an electrical potential difference is applied between the substrate and a liquid in contact with the second layer of from about 1200 volts to about 5000 volts.

53. The method of claim 52, wherein the device is an effective moisture and ion barrier when the electrical potential difference between the substrate and the liquid is about 4300 volts.

54. The method of claim 52, wherein the device is an effective moisture and ion barrier when the electrical potential difference between the substrate and the liquid is about 1200 volts.

55. The method of claim 50, wherein the second layer comprises silicon oxynitride having a Refractive Index of from about 1.6 to about 1.8.

56. The method of claim 50, wherein the insulating material is a 2.5 $\mu$m film of oxide and the second layer is a 1 $\mu$m film of silicon oxynitride.

57. The method of claim 50, wherein the combined thickness of the film insulating material and the second layer is 1 $\mu$m or less thick.

58. The method of claim 50, wherein the device is an effective moisture and ion barrier when a liquid is in contact with the second layer and a voltage is applied for at least thirty seconds such that there is an electrical potential difference between the substrate and the liquid.

59. The method of claim 50, wherein the combined thickness of the first layer and the second layer is from about 0.1 microns to about 10 microns.

60. The method of claim 50, wherein the condensed film second layer is deposited conformally using low pressure chemical vapor deposition (LPCVD).

* * * * *